US011021490B2

(12) United States Patent
Patil et al.

(10) Patent No.: US 11,021,490 B2
(45) Date of Patent: Jun. 1, 2021

(54) PYRIDINIUM OXAZOLE DYAD SCAFFOLD AND A PROCESS FOR PREPARATION THEREOF

(71) Applicant: COUNCIL OF SCIENTIFIC AND INDUSTRIAL RESEARCH, New Delhi (IN)

(72) Inventors: Nitin Tukaram Patil, Maharashtra (IN); Aslam Chandbhai Shaikh, Maharashtra (IN); Prasad Padmakar Kulkarni, Maharashtra (IN); Dnyanesh Sadanand Ranade, Maharashtra (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 16/802,335

(22) Filed: Feb. 26, 2020

(65) Prior Publication Data

US 2020/0190108 A1 Jun. 18, 2020

Related U.S. Application Data

(62) Division of application No. 16/343,260, filed as application No. PCT/IN2017/050480 on Oct. 17, 2017, now Pat. No. 10,711,012.

(30) Foreign Application Priority Data

Oct. 18, 2016 (IN) .............................. 201611035581

(51) Int. Cl.
| | |
|---|---|
| *C07D 498/06* | (2006.01) |
| *C07D 471/06* | (2006.01) |
| *C07D 513/06* | (2006.01) |
| *B01J 31/18* | (2006.01) |

(52) U.S. Cl.
CPC ........ *C07D 498/06* (2013.01); *B01J 31/1845* (2013.01); *C07D 471/06* (2013.01); *C07D 513/06* (2013.01); *B01J 2531/824* (2013.01)

(58) Field of Classification Search
CPC ... C07D 498/06; C07D 471/06; C07D 513/06
USPC ........................................................ 546/62
See application file for complete search history.

(56) References Cited

U.S. PATENT DOCUMENTS

2011/0013620 A1 6/2011 Mao et al.

FOREIGN PATENT DOCUMENTS

| KR | 2017506 | * | 1/2006 |
|---|---|---|---|
| WO | 2007/009101 A2 | | 1/2007 |

OTHER PUBLICATIONS

Shinde et al., Chemical communications (2016), 52(52), 8152-8155.*
Tian et al., Nature Communications (2015), 6, 7472pp, p. 1-7.*
Dix et al., European Journal of Organic Chemistry (2002), (15), 2547-2556.*
Fortage et al. "Molecular Dyads of Ruthenium(II)-or Osmium(II)-Bis(terpyridine) Chromophores and Expanded Pyridinium Acceptors: Equilibration between MLCT and Charge-Separated Excited States", Inorganic Chemistry, vol. 52, No. 20, 2013, pp. 11944-11955, XP002776219.
International Search Report and Written Opinion dated May 24, 2018 issued in International Application No. PCT/IN2017/050480.
Shaikh et al. "Oxidative Intramolecular 1,2-Amino-Oxygenation of Alkynes under AuI/AuIII-Catalysis: Discovery of Pyridinium-Oxazole Dyad as an Ionic Fluorophore", Angewandte Chemie, International Edition, vol. 56, No. 3, Jan. 16, 2017 (Jan. 16, 2017), pp. 757-761, XP002776221.
Shinde et al. "Efficient access to alkynylated quinalizinones via the gold(I)-catalyzed aminoalkynylation of alkynes", Chemical Communications, vol. 52, No. 52, Jul. 4, 2016 (Jul. 4, 2016), pp. 8152-8155, XP002776220, Cambridge, United Kingdom.

* cited by examiner

*Primary Examiner* — Niloofar Rahmani
(74) *Attorney, Agent, or Firm* — Arent Fox LLP

(57) ABSTRACT

The present invention relates to a pyridinium oxazole dyad scaffold of formula (I) and a process for the preparation thereof. The present invention further discloses a pyridine compound of formula (II) which is used for the preparation of formula (I) and a process for preparation thereof.

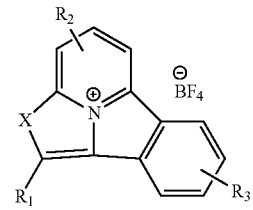

Formula (I)

4 Claims, 2 Drawing Sheets
(1 of 2 Drawing Sheet(s) Filed in Color)

PYRIDINIUM OXAZOLE DYAD SCAFFOLD AND A PROCESS FOR PREPARATION THEREOF

CROSS-REFERENCE TO RELATED APPLICATIONS

This application is a divisional of U.S. application Ser. No. 16/343,260 filed Apr. 18, 2019, which is a 35 U.S.C. § 371 National Phase of PCT Application No. PCT/IN2017/050480 filed Oct. 17, 2017, which claims priority to Indian Application No. 201611035581 filed Oct. 18, 2016. The disclosures of these applications are incorporated in their entireties herein by reference.

FIELD OF THE INVENTION

The present invention relates to a Pyridinium oxazole dyad scaffold of formula (I) and a process for the preparation thereof.

BACKGROUND AND PRIOR ART OF THE INVENTION

The discovery and development of organic fluorophores is essential for progress in many areas of chemistry, biology and functional materials research. As an emerging subclass, fluorescent organic salts are gaining much attention because of their unique properties. Because of their charged nature, they impart high thermal stabilities, phase tunabilities, water-solubility and chemoselective sensing via electrostatic interactions. These unique features have inspired research in a number of areas including fundamental photophysical investigations, sensory materials, and novel materials for display applications, multiphoton excitation (MPE), nanoscopic fluorescent ionic liquids, and LEC cells. In recent years, the highly photostable, less susceptible to environmental change and high specificity bearing a good photoactivatable fluorophore are powerful tools in biochemical and biological research such as cell lineage in development, macromolecule tracking in living cells, and super-resolved fluorescence imaging such as photoactivated localization microscopy (PALM), stochastic optical reconstruction microscopy (STORM), etc. Tracking cell organelles like the dynamics of mitochondrial morphology has attracted much research interest because of its involvement in early stage apoptosis and degenerative conditions. Therefore, developing a modular approach to novel organic emissive salts with tunable photophysical properties are highly warranted.

Over the last decade, homogeneous gold catalysis has emerged as a powerful tool for building molecular complexity in an atom-economical fashion. Gold catalysts act as it-acid and hence they are capable of activating unsaturated carbon-carbon bonds for the addition of nucleophiles (Scheme 1, path a). While manifestation of gold-catalyzed reactions are likely to be continued in the future, there is an urgent need to enable new modes of reactivities to expand gold-alkyne catalysis toolbox. In recent years, oxidative gold-catalyzed reactions have emerged as a new research field (path b). In 2007, Toste and Zhang independently reported gold(I)-catalyzed oxidative rearrangements of alkynyl sulfoxides which proceed via α-carbonyl gold-carbenoids formed through oxygen atom transfer from the sulfoxide. On the basis of this reactivity, the research groups of Liu, Davies, Ye, Zhang and others reported a variety of oxidative gold catalyzed reactions.

Yet another approach in the oxidative gold catalyzed reaction feature external oxidant-poared Au(I)/Au(III) catalysis, where the metal oxidation state changes during the catalytic cycle. A historical retrospect on the progress in the field of external oxidant-poared Au(I)/Au(III) catalysis reveals that the chemistry is either based on oxidative dimerization reactions of insitu gnerated vinylgold species (Scheme 1, eq 1) or cross-coupling reactions between respective substrates (eq 2). In recent years, gold-catalyzed aminoarylation/oxyarylation reaction of alkenes and arylboronic acids is emerging as new technique for heterocyclic synthesis (eq 3). Pioneering work from the group of Zhang and Muñiz reported the amination-arylation and diamination of alkenes via Au(I)/Au(III) catalysis (eq 4).

Article titled "Homogeneous Gold-Catalyzed oxidative carboheterofunctionalization of alkenes" by Guozhu Zhang et al. published in Journal of American Chemical Society, 2010, 132 (5), pp 1474-1475 reports Homogeneous carboamination, carboalkoxylation and carbolactonization of terminal alkenes are realized via oxidative gold catalysis, providing expedient access to various substituted N- or O-heterocycles. Deuterium-labeling studies established the antinature of the alkene functionalization and the indispensible role of Au(I)/Au(III) catalysis. This study constitutes the first example of catalytically converting C(sp3)-Au bonds into C(sp3)—C(sp2) bonds in a cross-coupling manner and opens new opportunities to study gold alkene catalysis where alkylgold intermediates can be readily functionalized intermolecularly.

Article titled "Au(I)/Au(III)-catalyzed Sonogashira-type reactions of functionalized terminal alkynes with arylboronic acids under mild conditions" by Deyun Qian et al. published in Beilstein Journal of Organic Chemistry, 2011; 7: 808-812 reports a straightforward, efficient, and reliable redox catalyst system for the Au(I)/Au(III)-catalyzed Sonogashira cross-coupling reaction of functionalized terminal alkynes with arylboronic acids under mild conditions has been developed.

Article titled "An efficient and recyclable magnetic-nanoparticle-supported Palladium catalyst for the Suzuki Coupling reactions of Organoboronic acids with Alkynyl Bromides" by Xiuli Zhang et al. published in Synthesis, 2011, 2975-2983 reports a highly active, air- and moisture-stable and easily recoverable magnetic-nanoparticle-supported palladium catalyst enables the Suzuki cross-coupling reaction of alkynyl bromides with organoboron derivatives in very good yields in ethanol. The supported palladium catalyst can be recovered and reused up to 16 times without significant loss of catalytic activity.

Article titled "Gold-catalyzed intramolecular aminoarylation of alkenes: C—C bond formation through bimolecular reductive elimination." by Brenzovich W E Jr et al. published in Angewandte Chemie International Edition, 2010 Jul. 26; 49(32):5519-22 reports Gold-catalyzed intramolecular aminoarylation of alkenes. Article titled "Gold-catalyzed carbon-heteroatom bond-forming reactions" by A. Corma et al. published in Chemical Reviews, 2011, 111, 1657-1712 reports gold-catalyzed transformations involving any carbon-heteroatom bond formation.

There exists no report on the di-functionalization of alkynes utilising Au(I)/Au(III) catalysis. There is need to develop tunable molecules for mitochondrial imaging and to develop intramolecular 1,2-aminooxygenation of alkynes to access pyridinium-oxazole dyad salts.

OBJECTIVES OF THE INVENTION

The main objective of the present invention is to provide a pyridinium oxazole dyad scaffold of formula (I) and a process for the preparation thereof.

Another objective of the present invention is to provide a pyridoalkyne compound of formula (II) and a process for the preparation thereof.

Still another objective of the present invention is to provide use of said Pyridinium oxazole dyad scaffold of formula (I).

SUMMARY OF THE INVENTION

Accordingly, the present invention provides a Pyridinium oxazole dyad scaffold of formula (I);

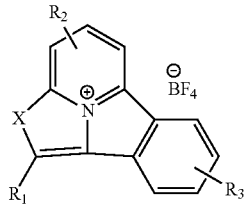

Formula (I)

Wherein; $R_1$, $R_2$ and $R_3$ are same or different and each is independently selected from the group consisting of H, alkyl groups, alkenyl groups, aryl groups, heteroaryl groups, electron donating as well as electron withdrawing substitutents;

X is selected from the group consisting of —CRR', O, S and —NR wherein R and R' are same or different and each is independently selected from the group consisting of H, alkyl, benzyl, and aryl; further R and R' may form a cyclic ring having 4 to 6 carbon atoms. The scaffold is used for imaging application for diagnosis of disease, wherein said imaging is mitochondrial imaging and said disease is cancer and said scaffold is used as a fluorescent agent for mitochondrial imaging.

In an embodiment, the present invention provides a pyridine compound of formula (II),

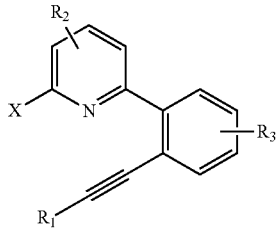

Formula (II)

Wherein; $R_1$, $R_2$ and $R_3$ are same or different and each is independently selected from the group consisting of H, alkyl groups, alkenyl groups, aryl groups, heteroaryl groups, electron donating as well as electron withdrawing substituents;

X is selected from the group consisting of H, alkyl, benzyl, aryl, —OR, —SR and —NR; wherein R is selected from the group consisting of H, alkyl and aryl In an embodiment, the present invention provides a process for the preparation of said Pyridinium oxazole dyad scaffold of formula (I) as claimed in claim 1, wherein said process comprises heating the reaction mixture consisting of pyridine of formula (II), in suitable solvent system in presence of gold catalyst at the temperature ranging from 70 to 80° C. for the time period ranging from 6 to 8 hours.

In an embodiment, the said solvent system is selected from group consisting of acetonitrile, dichloromethane, chloroform and toluene.

In an embodiment, the said gold catalyst is selected from group consisting of Chloro(triphenylphosphine)gold(I), Triphenylphosphine Gold(I) Trifluoromethanesulfonate, Chloro[(1,1'-biphenyl-2-yl)di-tert-butylphosphine]gold(I), Chloro-(2-Biphenyl)dicyclohexylphosphine gold(I), tBuCyJhonAuCl, Chloro-tris(4 fluro-triphenylphosphine) gold(I) (4-FC6H4)3P—AuCl, Chloro-tris(4 trifluromethyl-triphenylphosphine)gold(I) and Chloro-Tris(pentafluorophenyl)phosphine) gold (I).

In another embodiment, the present invention provides a process for the preparation of pyridine of formula (II) wherein said process comprising the steps of: degassing the reaction mixture consisting of pyridine derivative, boronic acid in suitable solvent with nitrogen; adding sodium carbonate or potassium carbonate, Palladium catalyst to the reaction mixture of step a under continuous flow of nitrogen; heating the reaction mixture of step b at the temperature ranging from 70 to 80° C. for 4 to 10 hours to afford desired product of formula (II).

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
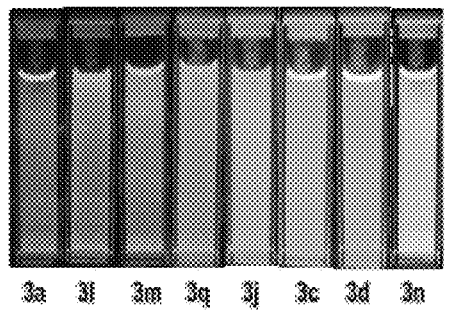
FIG. 1: Observed fluorescence under UV excitation (365 nm).

The invention will now be described in detail in connection with certain preferred and optional embodiments, so that various aspects thereof may be more fully understood and appreciated.

The present invention provides a pyridinium oxazole dyad scaffold of formula (I).

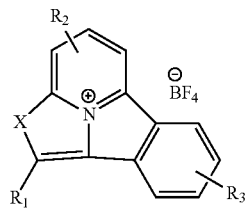

Formula (I)

Wherein; $R_1$, $R_2$ and $R_3$ are selected from the group consisting of H, alkyl groups, alkenyl groups, aryl groups, heteroaryl groups, such as electron donating as well as electron withdrawing substituents; $R_1$, $R_2$ and $R_3$ may be similar or different;

X=—CRR', O, S, —NR wherein R and R' are same or different and each is independently selected from the group consisting of H, alkyl, benzyl, or aryl; further R and R' may form a cyclic ring having 4 to 6 carbon atoms.

In preferred embodiment, said compound of formula I is tunable in UV region and Tunable emission wavelength depends upon substituents.

In an embodiment, the present invention provides pyridinium-oxazole dyad salts of formula (I) with tunable emission wavelengths.

In another embodiment of the present invention, said pyridinium-oxazole dyad salts of formula (I) can be accessed utilizing gold (I)-catalyzed oxidative intramolecular 1,2-aminoxygenation reactions, combining gold(I)/gold (III) catalysis.

In still another embodiment, the present invention provides intramolecular 1,2-aminooxygenation of alkynes to access pyridinium-oxazole dyad salts with tunable emission wavelengths.

In yet another embodiment, the present invention provides di-functionalization of alkynes utilising gold (I)/gold (III) catalysis.

In still yet another embodiment, the present invention provides a process for the preparation of a Pyridinium oxazole dyad scaffold of formula (I) comprises heating the reaction mixture consisting of pyridine of formula (II), Selectfluor in suitable solvent in presence of gold catalyst at the temperature ranging from 70 to 80° C. for the time period ranging from 6 to 8 hours to afford Pyridinium oxazole dyad scaffold.

In preferred embodiment, said pyridinium oxazole dyad scaffold of formula (I) are selected from 1-phenylbenzo[a]oxazolo[4,3,2-cd]indolizin-10-ium tetrafluoroborate, 1-(naphthalen-1-yl)benzo[a]oxazolo[4,3,2-cd]indolizin-10-iumtetrafluoroborate, 1-(naphthalen-2-yl)benzo[a]oxazolo[4,3,2-cd]indolizin-10-iumtetrafluoroborate, 1-(phenanthren-9-yl)benzo[a]oxazolo[4,3,2-cd]indolizin-10-ium tetrafluoroborate, 1-(p-tolyl)benzo[a]oxazolo[4,3,2-cd]indolizin-10-ium tetrafluoroborate, 1-(4-isopropylphenyl)benzo[a]oxazolo[4,3,2-cd]indolizin-10-ium tetrafluoroborate, 1-(4-pentylphenyl)benzo[a]oxazolo[4,3,2-cd]indolizin-10-ium tetrafluoroborate, 1-(4-methoxyphenyl)benzo[a]oxazolo[4,3,2-cd]indolizin-10-ium tetrafluoroborate, 1-(4-butoxyphenyl)benzo[a]oxazolo[4,3,2-cd]indolizin-10-ium, 1-(4-fluoro phenyl)benzo[a]oxazolo[4,3,2-cd]indolizin-10-iumtetrafluoroborate, 1-(4-chlorophenyl)benzo[a]oxazolo[4,3,2-cd]indolizin-10-iumtetrafluoroborate, 1-(4-(dimethylamino)phenyl) benzo[a]oxazolo[4,3,2-cd]indolizin-10-iumtetrafluoroborate, 1-(4-pentanoylphenyl) benzo[a]oxazolo[4,3,2-cd]indolizin-10-iumtetrafluoroborate, 1-(2-methoxyphenyl) benzo[a]oxazolo[4,3,2-cd]indolizin-10-iumtetrafluoroborate, 1-(3-methoxyphenyl)benzo[a]oxazolo[4,3,2-cd]indolizin-10-iumtetrafluoroborate, 1-(3-chlorophenyl)benzo[a]oxazolo[4,3,2-cd]indolizin-10-iumtetrafluoroborate, 6-methyl-1-phenylbenzo[a]oxazolo[4,3,2-cd]indolizin-10-ium tetrafluoroborate, 7-methyl-1-phenylbenzo[a]oxazolo[4,3,2-cd]indolizin-10-iumtetrafluoroborate, 7-fluoro-1-phenylbenzo[a]oxazolo[4,3,2-cd]indolizin-10-ium tetrafluoroborate, 7-chloro-1-phenylbenzo[a]oxazolo[4,3,2-cd]indolizin-10-ium tetrafluoroborate, 1-phenyldibenzo[a,f]oxazolo[4,3,2-cd]indolizin-12-ium tetrafluoroborate.

The scheme 1 is as shown below

Scheme 1

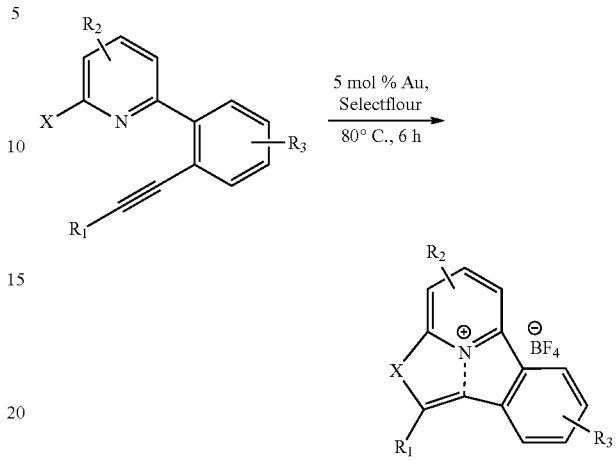

In another preferred embodiment, said solvent system is selected from acetonitrile ($CH_3CN$), dichloromethane ($CH_2Cl_2$), chloroform ($CHCl_3$) and toluene.

In still another preferred embodiment, said gold catalyst is selected from Chloro(triphenylphosphine)gold(I) ($PPh_3AuCl$), Triphenylphosphine Gold(I) Trifluoromethanesulfonate ($PPh_3AuOTf$), Chloro[(1,1'-biphenyl-2-yl)di-tert-butylphosphine]gold(I) (JohnPhosAuCl), Chloro-(2-Biphenyl)dicyclohexylphosphine gold(I) (CyJohnPhosAuCl), tBuCyJhonAuCl, Chloro-tris(4 fluro-triphenylphosphine) gold(I) ($4\text{-}FC_6H_4)_3P$—AuCl, Chloro-tris(4 trifluromethyl-triphenylphosphine)gold(I) $(4\text{-}CF_3C_6H_4)_3PAuCl$, Chloro-Tris(pentafluorophenyl)phosphine) gold (I) $(C_6F_5)_3P$—AuCl.

In still yet another embodiment, the present invention provides pyridine of formula (II) which is used for the preparation of formula (I).

Formula (II)

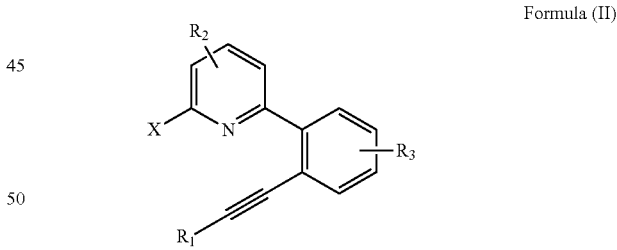

Wherein; $R_1$, $R_2$ and $R_3$ are selected from the group consisting of H, alkyl groups, alkenyl groups, aryl groups, heteroaryl groups, such as electron donating as well as electron withdrawing substituents; $R_1$, $R_2$ and $R_3$ may be similar or different;

X=H, alkyl, benzyl, aryl, —OR, —SR, —NR; wherein R=H, alkyl or aryl.

In a preferred embodiment, said compound of formula (II) are selected from 2-(tert-butoxy)-6-(2-(phenylethynyl)phenyl)pyridine, 2-(tert-butoxy)-6-(2-(naphthalen-1-ylethynyl) phenyl) pyridine, 2-(tert-butoxy)-6-(2-(naphthalen-2-ylethynyl)phenyl)pyridine, 2-(tert-butoxy)-6-(2-(phenanthren-9-ylethynyl)phenyl)pyridine, 2-(tert-butoxy)-6-(2-(hept-1-yn-1-yl)phenyl) pyridine, 2-(tert-butoxy)-6-(2-

(cyclohex-1-en-1-ylethynyl)phenyl)pyridine, 2-(tert-butoxy)-6-(2-(p-tolylethynyl)phenyl)pyridine, 2-(tert-butoxy)-6-(2-((4-isopropylphenyl)ethynyl) phenyl)pyridine, 2-(tert-butoxy)-6-(2-((4-pentylphenyl)ethynyl)phenyl)pyridine, 2-(tert-butoxy)-6-(2-((4-methoxyphenyl)ethynyl)phenyl)pyridine, 2-(tert-butoxy)-6-(2-((4-butoxyphenyl)ethynyl)phenyl)pyridine, 2-(tert-butoxy)-6-(2-((4-fluorophenyl)ethynyl)phenyl)pyridine, 2-(tert-butoxy)-6-(2-((4-chlorophenyl)ethynyl)phenyl)pyridine, 4-((2-(6-(tert-butoxy)pyridin-2-yl)phenyl)ethynyl)-N,N-dimethylaniline, 1-(4-((2-(6-(tert-butoxy)pyridin-2-yl)phenyl)ethynyl)phenyl)pentan-1-one, 2-(tert-butoxy)-6-(2-((2-methoxyphenyl)ethynyl)phenyl)pyridine, 2-(tert-butoxy)-6-(2-((3-methoxyphenyl)ethynyl)phenyl)pyridine, 2-(tert-butoxy)-6-(2-((3-chlorophenyl)ethynyl)phenyl)pyridine, 2-(tert-butoxy)-6-(2-methyl-6-(phenylethynyl)phenyl)pyridine, 2-(tert-butoxy)-6-(5-methyl-2-(phenylethynyl)phenyl)pyridine, 2-(tert-butoxy)-6-(5-fluoro-2-(phenylethynyl)phenyl) pyridine, 2-(tert-butoxy)-6-(5-chloro-2-(phenylethynyl)phenyl)pyridine, 2-(tert-butoxy)-6-(4-chloro-2-(phenylethynyl)phenyl) pyridine, 1-methoxy-3-(2-(phenylethynyl)phenyl) isoquinoline, 2-(tert-butoxy)-6-(2-((2-chloro-5-methoxyphenyl)ethynyl)phenyl)pyridine, 2-(tert-butoxy)-6-(2-((3-chloro-4-methylphenyl)ethynyl)phenyl)pyridine, 2-(tert-butoxy)-6-(3,5-dimethoxy-2-(phenylethynyl)phenyl)pyridine.

In still yet another embodiment, the present invention provides a process for the preparation of pyridine of formula (II) comprising the steps of
a) degassing the reaction mixture consisting of pyridine derivative, boronic acid in suitable solvent with nitrogen;
b) adding sodium carbonate or potassium carbonate, Palladium catalyst to the reaction mixture of step a under continuous flow of nitrogen;
c) heating the reaction mixture of step b at the temperature ranging from 70 to 80° C. for 4 to 10 hours to afford desired product of formula (II).

In preferred embodiment, said boronic acid of step (a) is 2-alkylnyl aryl boronic acid preferably 2-allkynyl phenyl boronic acid.

In another preferred embodiment, said solvent is DMF/H$_2$O in ratio 1:1.

In still another preferred embodiment, said Palladium catalyst of step (b) is PdCl$_2$(PPh)$_2$.

In yet another embodiment, the present invention provides use of said compound of formula I for imaging application, particularly mitochondrial imaging for diagnosis of cancer.

In a preferred embodiment, said compound of formula I is used as a fluorescent agent for mitochondrial imaging.

Figure 6:
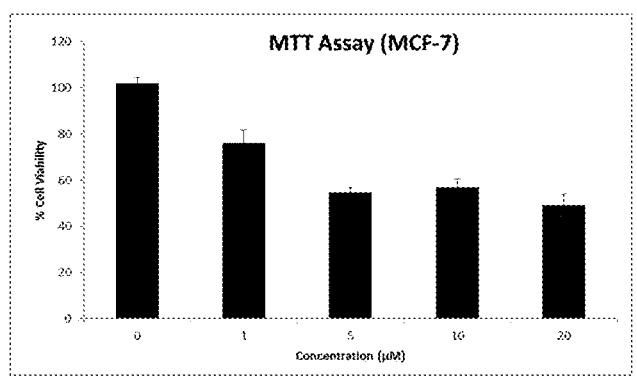
FIG. 6: MTT assay

In still yet another embodiment, the present invention provides cytotoxicity evaluation study of compound of formula I preferably 3n using a 3-(4,5-dimethyl-2-thiazolyl)-2,5-diphenyl tetrazolium bromide (MTT) assay (FIG. 6).

In still yet another embodiment, the present invention provides assessment of compound of formula I preferably 3n for its ability to localize and stain mitochondria in living cells by fluorescence microscope.

The novel compounds of the invention are brightly fluorescent. The compounds and the salts thereof are class of fluorescent materials containing a pyridinium-oxazole functional group.

The photo-physical properties of representative salts are studied in CH$_2$Cl$_2$ at RT (FIG. 1).

Figure 3:
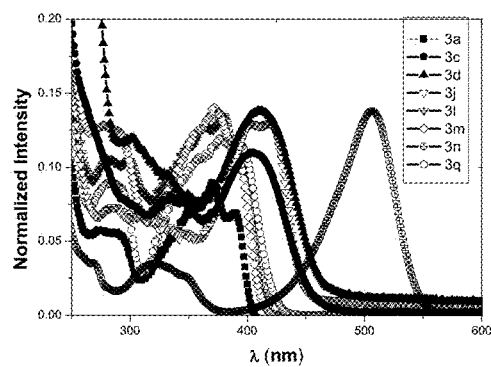
FIG. 3: Absorption of representative derivatives in DCM
Figure 4:
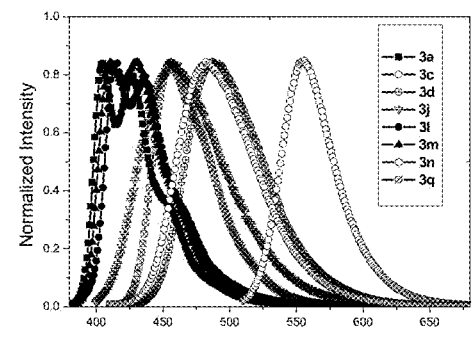
FIG. 4: Emission of representative derivatives in DCM at RT
Figure 5:
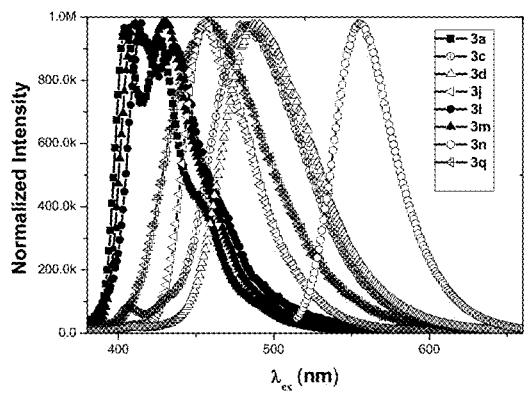
FIG. 5: Excitation of representative derivatives in DCM at RT

The corresponding absorption, emission and excitation, spectra are depicted in FIGS. 3, 4 and 5. The photoluminescence spectra of salts show intense peaks between λem: 400-560 nm (FIG. 1) with Stokes shifts varies between (30-80 nm) which reveals violet-to-yellow fluorescence emissions depending on the functional group present in the salts. The compounds display good quantum yields upto 0.76.

The novel compounds of the invention may be useful as Organic light emitting diodes (OLED) materials for solution processing.

Table 1 shows Spectral properties of representative derivatives in DCM at Room temperature (RM) (10-5 M)

TABLE 1

Spectral properties of representative derivatives in DCM at RM (10–5M)

| Comp | $\lambda_{abs}$ (nm)$^a$ | $\lambda_{em}$ (nm)$^b$ | $\lambda_{ex}$ (nm)$^c$ | $\Delta_{Stokes}$ (nm)$^d$ | $\phi_f^e$ | $\tau_f$ (nm)$^f$ |
|---|---|---|---|---|---|---|
| 3a | 368 | 404 | 338 | 036 | 0.10 | 1.2 |
| 3m | 370 | 410 | 339 | 040 | 0.19 | 1.7 |
| 3l | 372 | 414 | 343 | 042 | 0.09 | 0.9 |
| 3q | 376 | 455 | 332 | 079 | 0.20 | 2.0 |
| 3j | 405 | 458 | 338 | 053 | 0.42 | 2.4 |
| 3c | 410 | 481 | 364 | 071 | 0.49 | 5.2 |
| 3d | 411 | 487 | 365 | 076 | 0.54 | 7.2 |
| 3n | 506 | 555 | 511 | 049 | 0.76 | 9.1 | a The maximum absorption bands more than 300 nm; b Excited at the longest maximum absorption band in CH$_2$Cl$_2$; $^c$Excited wavelength; $^d$Stokes shift=λem–λ$_{abs}$; $^e$Quinine sulfate and rhodamine 6G was used as the standard; $^f$Fluorescent lifetime The current invention provides compounds that display brightly fluorescence as well as a good $\phi_f$. The salts are a novel class of fluorescent materials that contain a pyridinium-oxazole functional group and the photo-physical properties of representative salts are studied in CH$_2$Cl$_2$ at RT The absorption and excitation maxima, the photoluminescence (PL) maxima and quantum yields (FF), as well as the excited state lifetimes (t$_f$) of these compounds in CH$_2$Cl$_2$ solution are listed in Tables 3, whereas the corresponding absorption, emission, excitation spectra are depicted in FIGS. 3, 4 and 5. The photoluminescence spectra of salts show intense peaks between λ$_{em}$: 400-560 nm (Table 3) with Stokes shifts varies between (30-80 nm) which reveals violet-to-yellow fluorescence emissions depending on the functional group present in the salts. Substituents like chloro and fluoro on the core had only a modest effect on the fluorescent properties (3l and 3j). When phenyl ring replaced by bulky substituents like 2-napthyl and 9-phenathryl on the core had stronger effect on the fluorescent properties (3c and 3d). The presence of stronger donar group like —NMe$_2$ leads to significant bathochromic shifts in emission (4a and 4h, and FIG. 1). These observations are indicative of a predominant π-π* character for the lowest excited state, and the life time t$_f$ values are consistent with a singlet multiplicity. Most of these compounds display good quantum yields upto 0.76 (3n). The radiative rate constants are barely affected by the substitution pattern, an indication of the similar excited state character for all compounds.

EXAMPLES

Following examples are given by way of illustration therefore should not be construed to limit the scope of the invention.

Example 1: General Procedure for Sonogashira Cross Coupling of Aryl Iodides with Different Substituted Acetylenes A suspension of (un)substituted 2-bromoiodobenzene (2 gm, 7.06 mmol), $PdCl_2(PPh_3)_2$ (99.2 mg, 0.14 mmol, 2 mol %), Cu(I) iodide (40.2 mg, 0.21 mmol, 3 mol %) in 20 mL of triethylamine was degassed three times. After 10 min a solution of (un)substituted aryl/alkyl acetylene (0.84 mL, 7.77 mmol, 1.1 eq) in $Et_3N$ (3.6 mL) is added dropwise over 5 min via syringe and the reaction mixture is left to stir for 12 h and monitored by TLC. After total consumption of the 2-bromoiodobenzene, the reaction mixture was filtered through celite and extracted with EtOAc (3×10 mL). The organic layer was washed with a saturated solution of $NH_4Cl$ (2×10 mL), water (2×10 mL), dried over $Na_2SO_4$ and the solvent was removed under vacuo. The reaction mixture was purified by flash chromatography on silica gel, (eluent: pet. ether) to give the product (un)substituted bromo benzene as a yellow oil (S1, Yield 88%).

Example 2: General Procedure for Preparation of 2-Alkynylphenylboronic Acids In a two-necked round bottom flask, 1.6 M solution of "BuLi in" hexanes (5.5 mL, 8.78 mmol, 1.5 eq) was added dropwise to a solution of 2-phenylethynyl bromobenzene ($S_1$) (1.5 g, 5.85 mmol) in 45 mL of diethyl ether under nitrogen atmosphere at −78° C. The mixture was stirred at −78° C. for 1 h and then at −40° C. for 1 h then cooled back to −78° C. and $B(O^iPr)_3$ (1.65 g, 8.78 mmol, 1.5 eq) is added dropwise. The mixture was allowed to warm up gradually to room temperature, while maintaining vigorous stirring for 16 h. Then, the reaction is quenched with 40 mL of 1N HCl for 30 minutes and extracted with EtOAc (3×20 mL). The combined organic solution is dried over $Na_2SO_4$ and the solvent was removed under vacuo. The product was purified by flash chromatography on silica gel, (eluent: pet. ether/EtOAc) followed by recrystallization from pet. ether to give the product (2-(phenylethynyl)phenyl)boronic acid ($S_{27}$) as a white solid (Yield 84%).

Example 3: General Procedure for Preparation of Suzuki Coupling Reaction Between Bromo-Pyridines and Boronic Acids In a sealed tube 2-bromo-6-$^t$butylypyridine (300 mg, 1.59 mmol) and (2-(phenylethynyl)phenyl)boronic acid ($S_{20}$) (425 mg, 1.91 mmol, 1.2 eq) in $DMF/H_2O$ 1:1 (2 mL) was degassed with nitrogen for 5 min followed by addition of $Na_2CO_3$ (507 mg, 4.78 mmol, 3 eq) under continuous flow of nitrogen, $PdCl_2(PPh_3)_2$ (55.8 mg, 0.079 mmol, 5 mol %) were added to the reaction mixture under a nitrogen atmosphere. The reaction mixture was stirred at 80° C. for 12 h the solution was diluted with $NaHCO_3$ (5 mL), and then the product is extracted with EtOAc (3×05 mL). The combined organic layer was dried over $Na_2SO_4$ and the solvent is removed under vacuo. The crude product was purified on a silica gel column using pet. ether/EtOAc as eluent to afford 2-methoxy-6-(2 (phenylethynyl)-phenyl) pyridine (1a) as a yellow thick liquid (Yield 84%).

a) 2-(tert-butoxy)-6-(2-(phenylethynyl)phenyl)pyridine (1a)

Thick liquid, 84% yield; $R_f$=0.80 (Pet.Ether/EtOAc=95/05); $^1$H NMR (500 MHz, $CDCl_3$) δ=7.88 (d, J=7.6 Hz, 1H), 7.74-7.67 (m, 2H), 7.67-7.61 (m, 1H), 7.50-7.43 (m, 3H), 7.42-7.37 (m, 1H), 7.37-7.30 (m, 3H), 6.70 (d, J=8.0 Hz, 1H), 1.69 (s, 9H); $^{13}$C NMR (125 MHz, $CDCl_3$) δ=163.4, 154.2, 142.2, 137.8, 133.2, 131.4, 129.7, 128.4, 128.3, 128.2, 127.7, 123.5, 121.0, 116.6, 111.8, 92.6, 89.6, 79.4, 28.8; HRMS (ESI) calcd for $C_{23}H_{12}ON$ (M$^+$+H) 328.1696, found 328.1694.

b) 2-(tert-butoxy)-6-(2-(naphthalen-1-ylethynyl)phenyl)pyridine (1b)

Yellowish solid, 78% yield; mp=108-109° C.; $R_f$=0.85 (Pet.Ether/EtOAc=95/05); $^1$H NMR (500 MHz, $CDCl_3$) δ=8.28-8.21 (m, 1H), 7.98-7.94 (m, 1H), 7.92-7.85 (m, 3H), 7.81 (d, J=7.2 Hz, 1H), 7.78-7.74 (m, 1H), 7.69 (t, J=7.8 Hz, 1H), 7.59-7.53 (m, 3H), 7.52-7.46 (m, 2H), 6.82 (d, J=8.0 Hz, 1H), 1.75 (s, 9H); $^{13}$C NMR (125 MHz, $CDCl_3$) δ=163.6, 154.6, 142.5, 138.1, 133.3, 133.2, 133.1, 130.2, 129.7, 128.6, 128.5, 128.1, 127.8, 126.6, 126.3, 125.2, 121.3, 121.1, 116.8, 111.8, 94.3, 90.9, 79.5, 77.3, 76.7, 28.8; HRMS (ESI) calcd for $C_{27}H_{24}ON$ (M$^+$+H) 378.1852, found 378.1850.

c) 2-(tert-butoxy)-6-(2-(phenanthren-9-ylethynyl)phenyl)pyridine (1d)

Yellowish solid, 68% yield; mp=86-87° C.; $R_f$=0.85 (Pet.Ether/EtOAc=95/05); $^1$H NMR (500 MHz, $CDCl_3$) δ=8.66 (d, J=8.4 Hz, 1H), 8.69 (d, J=8.4 Hz, 1H), 8.24 (d, J=8.4 Hz, 1H), 7.99 (s, 1H), 7.90-7.80 (m, 3H), 7.73 (d, J=7.2 Hz, 1H), 7.71-7.55 (m, 6H), 7.53-7.48 (m, 1H), 7.47-7.41 (m, 1H), 6.74 (d, J=8.0 Hz, 1H), 1.66 (s, 9H); $^{13}$C NMR (125 MHz, $CDCl_3$) δ=163.6, 154.6, 142.6, 138.1, 133.4, 131.7, 131.2, 131.1, 130.2, 130.0, 129.8, 128.5, 127.8, 127.4, 127.1, 127.0, 126.9, 122.7, 122.6, 121.3, 119.9, 116.8, 111.9, 93.9, 91.1, 79.6, 28.9; HRMS (ESI) calcd for $C_{31}H_{26}ON$ (M$^+$+H) 428.2009, found 428.2007.

d) 2-(tert-butoxy)-6-(2-(hept-1-yn-1-yl)phenyl)pyridine (1e)

Thick liquid, 56% yield; $R_f$=0.70 (Pet.Ether/EtOAc=95/05); $^1$H NMR (500 MHz, $CDCl_3$) δ=7.82 (dd, J=1.1, 7.6 Hz, 1H), 7.66 (d, J=6.9 Hz, 1H), 7.60-7.53 (m, 2H), 7.40 (dt, J=1.1, 7.6 Hz, 1H), 7.34-7.28 (m, 1H), 6.66 (d, J=7.6 Hz, 1H), 2.40 (t, J=7.1 Hz, 2H), 1.69 (s, 9H), 1.43-1.34 (m, 4H), 0.94 (t, J=7.2 Hz, 3H); $^{13}$C NMR (125 MHz, $CDCl_3$) δ=163.3, 154.5, 141.9, 137.7, 133.4, 129.6, 127.6, 127.5, 121.8, 116.5, 111.5, 93.9, 80.5, 79.3, 31.1, 28.8, 28.1, 22.2, 19.6, 14.0; HRMS (ESI) calcd for $C_{22}H_{28}ON$ (M$^+$+H) 322.2165, found 322.2165.

e) 2-(tert-butoxy)-6-(2-(p-tolylethynyl)phenyl)pyridine (1g)

Thick liquid, 82% yield; $R_f$=0.80 (Pet.Ether/EtOAc=95/05); $^1$H NMR (500 MHz, $CDCl_3$) δ=7.90-7.82 (m, 1H), 7.70 (d, J=7.2 Hz, 1H), 7.68-7.64 (m, 1H), 7.64-7.59 (m, 1H), 7.47-7.42 (m, 1H), 7.39-7.31 (m, 3H), 7.15 (d, J=8.0 Hz, 2H), 6.67 (d, J=8.0 Hz, 1H), 2.37 (s, 3H), 1.66 (s, 9H); 13C NMR (125 MHz, $CDCl_3$) δ=163.4, 154.3, 142.1, 138.3, 137.8, 133.2, 131.3, 129.7, 129.1, 128.2, 127.7, 121.2, 120.4, 116.6, 111.7, 92.8, 89.0, 79.4, 28.9, 21.5; HRMS (ESI) calcd for $C_{24}H_{24}ON$ (M$^+$+H) 342.1852, found 342.1852.

f) 2-(tert-butoxy)-6-(2-((4-methoxyphenyl)ethynyl)phenyl)pyridine (1j)

Thick liquid, 76% yield; $R_f$=0.70 (Pet.Ether/EtOAc=95/05); $^1$H NMR (500 MHz, CDCl$_3$) δ=7.91-7.82 (m, 1H), 7.72 (d, J=7.2 Hz, 1H), 7.69-7.60 (m, 2H), 7.48-7.42 (m, 1H), 7.42-7.34 (m, 3H), 6.88 (d, J=8.8 Hz, 2H), 6.69 (d, J=8.0 Hz, 1H), 3.82 (s, 3H), 1.68 (s, 9H); 13C NMR (125 MHz, CDCl$_3$) δ=163.4, 159.6, 154.3, 142.0, 137.8, 133.0, 132.8, 129.7, 128.1, 127.7, 121.3, 116.6, 115.6, 113.9, 111.7, 92.6, 88.3, 79.4, 55.2, 28.8; HRMS (ESI) calcd for C$_{24}$H$_{24}$O$_2$N (M$^+$+H) 358.1802, found 358.1801.

g) 2-(tert-butoxy)-6-(2-((4-fluorophenyl)ethynyl)phenyl)pyridine (1l)

Thick liquid, 65% yield; $R_f$=0.70 (Pet.Ether/EtOAc=95/05); $^1$H NMR (500 MHz, CDCl$_3$) δ=7.87-7.81 (m, 1H), 7.68-7.60 (m, 3H), 7.49-7.44 (m, 1H), 7.44-7.34 (m, 3H), 7.07-6.98 (m, 2H), 6.68 (dd, J=1.9, 7.0 Hz, 1H), 1.66 (s, 9H); 13C NMR (125 MHz, CDCl$_3$) δ=163.5, 163.4-161.4 (d, J=248.91 Hz), 154.3, 142.3, 137.8, 133.3-133.1 (d, J=14.31 Hz), 133.2, 129.8, 128.5, 127.7, 120.8, 119.6-119.6 (d, J=2.86 Hz), 116.5, 115.7-115.5 (d, J=21.94 Hz), 111.8, 91.4, 89.3, 79.5, 28.8; HRMS (ESI) calcd for C$_{23}$H$_{21}$ONF (M$^+$+H) 346.1602, found 346.1600.

h) 4-((2-(6-(tert-butoxy)pyridin-2-yl)phenyl)ethynyl)-N,N-dimethylaniline (1n)

Yellowish solid, 68% yield; mp=116-117° C.; $R_f$=0.65 (Pet.Ether/EtOAc=95/05); $^1$H NMR (500 MHz, CDCl$_3$) δ=7.86 (d, J=7.6 Hz, 1H), 7.77 (d, J=6.9 Hz, 1H), 7.67-7.59 (m, 2H), 7.45-7.38 (m, 1H), 7.37-7.29 (m, 3H), 6.66 (d, J=9.2 Hz, 3H), 2.99 (s, 6H), 1.67 (s, 9H); $^{13}$C NMR (125 MHz, CDCl$_3$) δ=163.4, 154.4, 150.0, 141.5, 137.8, 132.8, 132.5, 129.6, 127.6, 127.6, 121.9, 116.7, 111.8, 111.5, 110.3, 94.0, 87.7, 79.3, 40.2, 28.9; HRMS (ESI) calcd for C$_{25}$H$_{27}$ON$_2$ (M$^+$+H) 371.2118, found 371.2117.

i) 1-(4-((2-(6-(tert-butoxy)pyridin-2-yl)phenyl)ethynyl)phenyl)pentan-1-one (1o)

Thick liquid, 58% yield; $R_f$=0.60 (Pet.Ether/EtOAc=95/05); $^1$H NMR (500 MHz, CDCl$_3$) δ=7.92 (d, J=8.3 Hz, 2H), 7.83 (d, J=7.3 Hz, 1H), 7.67 (d, J=7.8 Hz, 1H), 7.62 (q, J=7.7 Hz, 2H), 7.52-7.42 (m, 3H), 7.42-7.31 (m, 1H), 6.68 (d, J=7.3 Hz, 1H), 1.77-1.69 (m, 2H), 1.65 (s, 9H), 1.46-1.38 (m, 2H), 0.97 (t, J=7.3 Hz, 3H); 13C NMR (125 MHz, CDCl$_3$) δ=199.7, 163.5, 154.1, 142.6, 137.9, 136.0, 133.3, 131.4, 129.8, 128.9, 128.1, 127.9, 127.8, 120.4, 116.5, 111.9, 92.9, 91.7, 79.5, 77.3, 76.7, 38.3, 28.8, 26.4, 22.4, 13.9; HRMS (ESI) calcd for C$_{28}$H$_{30}$O$_2$N (M$^+$+H) 412.2271, found 412.2268.

j) 2-(tert-butoxy)-6-(5-methyl-2-(phenylethynyl)phenyl)pyridine (1t)

Thick liquid, 72% yield; $R_f$=0.80 (Pet.Ether/EtOAc=95/05); $^1$H NMR (400 MHz, CDCl$_3$) δ=7.70-7.61 (m, 3H), 7.59 (d, J=7.8 Hz, 1H), 7.49-7.39 (m, 2H), 7.38-7.29 (m, 3H), 7.21 (d, J=7.8 Hz, 1H), 6.69 (d, J=7.8 Hz, 1H), 2.47 (s, 3H), 1.69 (s, 9H); 13C NMR (100 MHz, CDCl$_3$) δ=163.4, 154.5, 142.1, 138.4, 137.8, 133.2, 131.3, 130.4, 128.6, 128.2, 128.0, 123.7, 118.1, 116.7, 111.7, 91.8, 89.8, 79.4, 77.3, 76.7, 28.9, 21.6; HRMS (ESI) calcd for C$_{24}$H$_{24}$ON (M$^+$+H) 342.1852, found 342.1851.

k) 2-(tert-butoxy)-6-(5-fluoro-2-(phenylethynyl)phenyl)pyridine (1u)

Thick liquid, 74% yield; mp=65-66° C.; $R_f$=0.70 (Pet.Ether/EtOAc=95/05); $^1$H NMR (400 MHz, CDCl$_3$) δ=7.77 (d, J=7.3 Hz, 1H), 7.69-7.57 (m, 3H), 7.51-7.41 (m, 2H), 7.39-7.28 (m, 3H), 7.09 (dt, J=2.4, 8.2 Hz, 1H), 6.71 (d, J=7.9 Hz, 1H), 1.68 (s, 9H); $^{13}$C NMR (100 MHz, CDCl$_3$) δ=163.7-161.3 (d, J=248.92 Hz), 163.5, 152.8, 144.5-144.4 (d, J=8.48 Hz), 138.0, 135.2-135.1 (d, J=8.48 Hz), 131.3, 128.3, 128.2, 123.3, 117.0 (d, J=3.03 Hz), 116.7-116.4 (d, J=23.12 Hz), 116.5, 115.2-115.0 (d, J=21.58 Hz), 112.4, 92.3, 88.7, 79.6, 28.8; HRMS (ESI) calcd for C$_{23}$H$_{21}$ONF (M$^+$+H) 346.1602, found 346.1601.

l) 1-methoxy-3-(2-(phenylethynyl)phenyl)isoquinoline (1x)

During preparation of 1x, the 2-bromo-6-methoxyisoquinoline was used instead of 2-bromo-6-butylypyridine.

Yellowish solid, 68% yield; mp=84-85° C.; $R_f$=0.75 (Pet.Ether/EtOAc=95/05); $^1$H NMR (400 MHz, CDCl$_3$) δ=8.35 (d, J=7.6 Hz, 1H), 8.16 (s, 1H), 8.09 (dd, J=1.1, 7.6 Hz, 1H), 7.84 (d, J=8.0 Hz, 1H), 7.77 (dd, J=1.1, 7.6 Hz, 1H), 7.70 (dt, J=1.3, 7.5 Hz, 1H), 7.59 (ddd, J=1.0, 7.0, 8.1 Hz, 1H), 7.54-7.50 (m, 1H), 7.50-7.45 (m, 2H), 7.42 (dt, J=1.3, 7.5 Hz, 1H), 7.36-7.32 (m, 3H), 4.27 (s, 3H); $^{13}$C NMR (100 MHz, CDCl$_3$) δ=160.2, 147.5, 141.9, 138.2, 133.5, 131.3, 130.4, 129.8, 128.5, 128.3, 128.1, 127.6, 126.6, 126.6, 124.1, 123.6, 121.1, 118.8, 115.0, 92.7, 90.0, 53.7; HRMS (ESI) calcd for C$_{28}$H$_{18}$ON (M$^+$+H) 336.1383, found 336.1384.

m) 2-(tert-butoxy)-6-(2-((2-chloro-5-methoxyphenyl)ethynyl)phenyl)pyridine (1y)

Yellowish solid, 52% yield; mp=85-86° C.; $R_f$=0.60 (Pet.Ether/EtOAc=95/05); $^1$H NMR (500 MHz, CDCl$_3$) δ=7.87 (dd, J=1.1, 8.0 Hz, 1H), 7.75 (d, J=7.2 Hz, 1H), 7.72 (dd, J=1.1, 7.6 Hz, 1H), 7.63-7.57 (m, 1H), 7.48 (dt, J=1.5, 7.6 Hz, 1H), 7.41-7.35 (m, 1H), 7.28 (d, J=8.8 Hz, 1H), 6.96 (d, J=3.1 Hz, 1H), 6.81 (dd, J=3.1, 8.8 Hz, 1H), 6.66 (d, J=8.4 Hz, 1H), 3.79 (s, 3H), 1.65 (s, 9H); $^{13}$C NMR (125 MHz, CDCl$_3$) δ=163.4, 157.8, 153.9, 142.3, 138.0, 133.7, 129.9, 129.7, 128.9, 127.7, 127.4, 123.9, 120.6, 117.6, 116.9, 116.0, 111.9, 94.3, 89.5, 79.4, 55.5, 28.8; HRMS (ESI) calcd for C$_{24}$H$_{22}$O$_2$NCl (M$^+$+H) 392.1412, found 392.1417.

n) 2-(tert-butoxy)-6-(2-((3-chloro-4-methylphenyl)ethynyl)phenyl)pyridine (1z)

Yellowish solid, 52% yield; mp=81-82° C.; $R_f$=0.60 (Pet.Ether/EtOAc=95/05); $^1$H NMR (500 MHz, CDCl$_3$) δ=7.67-7.61 (m, 3H), 7.46 (dt, J=1.5, 7.6 Hz, 1H), 7.42 (d, J=1.5 Hz, 1H), 7.37 (dt, J=1.1, 7.4 Hz, 1H), 7.23-7.15 (m, 2H), 6.68 (t, J=4.4 Hz, 1H), 2.39 (s, 3H), 1.66 (s, 9H); 13C NMR (125 MHz, CDCl$_3$) δ=163.5, 154.2, 142.3, 137.9, 136.4, 134.2, 133.2, 131.6, 130.8, 129.8, 129.5, 128.6, 127.7, 122.4, 120.7, 116.5, 111.9, 91.2, 90.1, 79.5, 28.9, 20.0; HRMS (ESI) calcd for C$_{24}$H$_{23}$ONCl (M$^+$+H) 376.1463, found 376.1458.

o) 2-(tert-butoxy)-6-(3,5-dimethoxy-2-(phenylethynyl)phenyl)pyridine (1aa)

Yellowish solid, 76% yield; mp=124-125° C.; $R_f$=0.55 (Pet.Ether/EtOAc=95/05); $^1$H NMR (400 MHz, CDCl$_3$)

δ=7.70 (d, J=7.8 Hz, 1H), 7.61 (t, J=7.6 Hz, 1H), 7.42 (d, J=6.4 Hz, 2H), 7.35-7.25 (m, 3H), 7.02 (d, J=2.0 Hz, 1H), 6.67 (d, J=8.3 Hz, 1H), 6.53 (d, J=2.0 Hz, 1H), 3.96 (s, 3H), 3.89 (s, 3H), 1.66 (s, 9H); 13C NMR (100 MHz, CDCl$_3$) δ=163.2, 161.8, 160.3, 154.1, 145.1, 137.8, 131.2, 128.1, 127.6, 124.1, 116.9, 111.9, 106.0, 98.3, 95.8, 85.6, 79.4, 56.2, 55.3, 28.8; HRMS (ESI) calcd for $C_{25}H_{26}O_3N$ (M$^+$+H) 388.1907, found 388.1904.

Example 3: Procedure for Gold-Catalyzed 1,2 amino-oxygenation of alkyne

To a screw-cap vial containing a stir bar were added 2-(tert-butoxy)-6-(2-(phenylethynyl)phenyl)pyridine (1a) (80 mg, 0.10 mmol), 5 mol % $(C_6F_5)_3$P—AuCl (7 mg, 5 mol %) and CH$_3$CN (2 mL). The reaction vial was fitted with a cap, evacuated and back filled with N$_2$ and heated at 80° C. for 6 h. When the reaction time was completed, the reaction mixture was allowed to cool at ambient temperature. The mixture was diluted with CH$_2$Cl$_2$ (10 mL) and filtered through a Celite pad and the Celite pad was washed several times with CH$_2$Cl$_2$ (50 mL). The combined filtrate was concentrated in vacuo and the resulting residue was purified by column chromatography on silica (DCM/MeOH; 95:5) to afford the products. 3a as off white solid in 92% yield.

a) 1-phenylbenzo[a]oxazolo[4,3,2-cd]indolizin-10-ium tetrafluoroborate (3a)

Off white solid, 92% yield; mp=192-193° C.; R$_f$=0.50 (DCM/MeOH=95/05); $^1$H NMR (500 MHz, DMSO-d$_6$) δ=8.89 (br. s., 2H), 8.83 (d, J=5.9 Hz, 2H), 8.65 (d, J=3.9 Hz, 1H), 8.37 (d, J=7.3 Hz, 2H), 8.16-7.99 (m, 2H), 7.92-7.81 (m, 3H); $^{13}$C NMR (100 MHz, DMSO-d$_6$) δ=150.4, 146.4, 142.6, 135.8, 133.9, 133.4, 132.7, 131.0, 130.5, 127.6, 127.0, 125.9, 124.6, 121.2, 117.0, 108.6; nB NMR (160 MHz, DMSO-d$_6$): δ−1.31; $^{19}$F NMR (470 MHz, DMSO-d$_6$): δ−148.22, −148.28 and secondary isotopic shift ($^{10}$B, $^{11}$B) of 0.055 ppm; HRMS (ESI) calcd for $C_{19}H_{12}ON^+$ (M$^+$-BF$_4^-$) 270.0913, found 270.0910.

b) 1-(naphthalen-1-yl)benzo[a]oxazolo[4,3,2-cd]indolizin-10-ium tetrafluoroborate (3b)

Light yellow solid, 68% yield; mp=198-200° C.; R$_f$=0.45 (DCM/MeOH=95/05); $^1$H NMR (500 MHz, DMSO-d$_6$) δ=8.95 (s, 1H), 8.84 (d, J=7.6 Hz, 1H), 8.73 (d, J=7.2 Hz, 1H), 8.49-8.37 (m, 3H), 8.28 (d, J=6.5 Hz, 1H), 8.07-7.92 (m, 5H), 7.88-7.77 (m, 3H); $^{13}$C NMR (125 MHz, DMSO-d$_6$) δ=149.8, 147.0, 142.7, 135.9, 134.1, 133.9, 133.5, 132.5, 130.9, 129.4, 129.3, 128.9, 127.7, 127.2, 126.1, 125.9, 124.6, 124.3, 123.0, 121.4, 117.0, 109.0; HRMS (ESI) calcd for $C_{23}H_{14}ON^+$ (M$^+$-BF$_4^-$) 320.1070, found 320.1065.

c) 1-(phenanthren-9-yl)benzo[a]oxazolo[4,3,2-cd]indolizin-10-ium tetrafluoroborate (3d)

Light yellow solid, 63% yield; mp=230-232° C.; R$_f$=0.50 (DCM/MeOH=95/05); $^1$H NMR (400 MHz, DMSO-d$_6$) δ=9.16 (d, J=8.3 Hz, 1H), 9.09-9.04 (m, 1H), 9.01-8.91 (m, 2H), 8.85 (d, J=7.8 Hz, 1H), 8.79 (s, 1H), 8.75 (d, J=7.8 Hz, 1H), 8.50 (d, J=7.8 Hz, 1H), 8.39 (d, J=7.8 Hz, 1H), 8.13-7.93 (m, 5H), 7.87 (q, J=7.5 Hz, 2H); $^{13}$C NMR (100 MHz, DMSO-d$_6$) δ=153.3, 149.6, 147.0, 142.9, 136.0, 134.2, 133.3, 132.6, 131.5, 130.9, 130.4, 130.3, 130.0, 128.6, 128.4, 128.1, 127.2, 125.9, 125.3, 124.9, 124.3, 123.5, 123.4, 123.2, 122.7, 120.6, 117.1, 115.6, 109.0; HRMS (ESI) calcd for $C_{27}H_{16}ON^+$ (M$^+$-BF$_4^-$) 370.1225, found 370.1226.

d) 1-(p-tolyl)benzo[a]oxazolo[4,3,2-cd]indolizin-10-ium tetrafluoroborate (3g)

Off white solid, 85% yield; mp=222-223° C.; R$_f$=0.40 (DCM/MeOH=95/05); $^1$H NMR (500 MHz, DMSO-d$_6$) δ=8.92-8.84 (m, 2H), 8.79 (d, J=8.0 Hz, 1H), 8.82 (d, J=8.0 Hz, 1H), 8.65-8.56 (m, 1H), 8.27 (d, J=8.0 Hz, 2H), 8.10 (t, J=7.4 Hz, 1H), 8.05 (t, J=7.6 Hz, 1H), 7.68 (d, J=7.6 Hz, 2H), 2.53 (s, 3H); $^{13}$C NMR (100 MHz, DMSO-d$_6$) δ=150.8, 146.2, 144.2, 142.2, 135.7, 133.7, 132.6, 131.0, 130.8, 127.6, 127.0, 125.8, 124.4, 121.8, 120.5, 116.9, 108.4, 21.4; HRMS (ESI) calcd for $C_{20}H_{14}ON^+$ (M$^+$-BF$_4^-$) 284.1070, found 284.1067.

e) 1-(4-isopropylphenyl)benzo[a]oxazolo[4,3,2-cd]indolizin-10-ium tetrafluoroborate (3h)

Off white solid, 80% yield; mp=214-215° C.; R$_f$=0.40 (DCM/MeOH=95/05); $^1$H NMR (400 MHz, DMSO-d$_6$) δ=8.88 (d, J=3.9 Hz, 2H), 8.79 (d, J=7.8 Hz, 1H), 8.82 (d, J=7.8 Hz, 1H), 8.63 (t, J=3.9 Hz, 1H), 8.36-8.23 (m, J=7.3 Hz, 2H), 8.13-8.02 (m, 2H), 7.78-7.70 (m, J=7.8 Hz, 2H), 3.12 (td, J=6.7, 13.6 Hz, 1H), 1.32 (d, J=7.3 Hz, 6H); $^{13}$C NMR (125 MHz, DMSO-d$_6$) δ=154.5, 150.8, 146.2, 142.3, 135.7, 133.8, 132.6, 130.8, 128.5, 127.9, 127.0, 125.9, 124.4, 122.2, 120.6, 116.9, 108.5, 33.7, 23.4; HRMS (ESI) calcd for $C_{22}H_{18}ON^+$ (M$^+$-BF$_4^-$) 312.1383, found 312.1382.

f) 1-(4-methoxyphenyl)benzo[a]oxazolo[4,3,2-cd]indolizin-10-ium tetrafluoroborate (3j)

Light yellow solid, 83% yield; mp=190-192° C.; R$_f$=0.30 (DCM/MeOH=95/10); $^1$H NMR (400 MHz, DMSO-d$_6$) δ=8.94-8.70 (m, 4H), 8.58 (d, J=7.3 Hz, 1H), 8.33 (d, J=8.5 Hz, 2H), 8.12-7.98 (m, 2H), 7.41 (d, J=8.5 Hz, 2H), 3.97 (br. s., 3H); 13C NMR (125 MHz, DMSO-d$_6$) δ=163.2, 151.1, 146.0, 141.7, 135.4, 133.5, 132.5, 130.5, 129.9, 127.1, 125.8, 124.0, 119.4, 116.7, 116.1, 108.1, 55.9; HRMS (ESI) calcd for $C_{20}H_{14}O_2N^+$ (M$^+$-BF$_4^-$) 300.1019, found 300.1019.

g) 1-(4-butoxyphenyl)benzo[a]oxazolo[4,3,2-cd]indolizin-10-ium tetrafluoroborate (3k)

Light yellow solid, 86% yield; mp=183-185° C.; R$_f$=0.30 (DCM/MeOH=95/10); $^1$H NMR (400 MHz, DMSO-d$_6$) δ=8.95-8.71 (m, 4H), 8.64-8.53 (m, 1H), 8.42-8.22 (m, 2H), 8.16-7.99 (m, 2H), 7.42-7.32 (m, 2H), 4.23-4.15 (m, 2H), 1.82-1.74 (m, 2H), 1.54-1.45 (m, 2H), 0.98 (t, J=7.3 Hz, 3H); $^{13}$C NMR (100 MHz, DMSO-d$_6$) δ=162.8, 151.2, 146.1, 141.7, 135.5, 133.5, 132.6, 130.5, 130.2, 130.0, 127.1, 125.8, 124.0, 119.4, 116.8, 116.5, 108.1, 68.130.6, 18.8, 13.8; HRMS (ESI) calcd for $C_{23}H_{20}O_2N^+$ (M$^+$-BF$_4^-$) 342.1489, found 342.1483.

h) 1-(4-fluorophenyl)benzo[a]oxazolo[4,3,2-cd]indolizin-10-ium tetrafluoroborate (3l)

Off white solid, 71% yield; mp=254-255° C.; R$_f$=0.60 (DCM/MeOH=95/10); $^1$H NMR (400 MHz, DMSO-d$_6$) δ=8.98-8.75 (m, 3H), 8.64 (d, J=8.3 Hz, 1H), 8.54-8.37 (m, 2H), 8.22-8.01 (m, 2H), 7.85-7.62 (m, 3H); $^{13}$C NMR (100 MHz, DMSO-d$_6$) δ=166.2, 165.9-163.4 (d, J=254.31 Hz), 153.1, 151.3, 149.5, 146.3, 143.7, 142.7, 135.8, 133.9, 132.9, 132.6, 131.6, 131.0, 130.9-130.8 (d, J=9.25 Hz), 130.7-130.6 (d, J=10.02 Hz), 126.9, 126.3, 126.0, 124.7, 124.4, 121.8, 121.3, 121.0, 118.2-118.0 (d, J=23.12 Hz), 118.1-117.9 (d, J=22.35 Hz), 117.1, 110.4-110.3 (d, J=6.94 Hz), 108.6; HRMS (ESI) calcd for $C_{19}H_{11}ONF^+$ ($M^+$-$BF_4^-$) 288.0819, found 288.0815.

i) 1-(4-chlorophenyl)benzo[a]oxazolo[4,3-cd]indolizin-10-ium tetrafluoroborate (3m)

Off white solid, 65% yield; mp=274-275° C.; $R_f$=0.60 (DCM/MeOH=95/10); $^1$H NMR (400 MHz, DMSO-$d_6$) δ=8.99-8.86 (m, 2H), 8.79 (d, J=7.3 Hz, 1H), 8.83 (d, J=7.8 Hz, 1H), 8.65 (d, J=6.8 Hz, 1H), 8.37 (d, J=8.3 Hz, 2H), 8.17-8.02 (m, 2H), 7.92 (d, J=8.3 Hz, 2H); $^{13}$C NMR (100 MHz, DMSO-$d_6$) δ=149.3, 146.4, 142.9, 138.0, 135.9, 134.0, 132.7, 131.2, 130.7, 129.4, 126.8, 126.0, 124.6, 123.4, 121.5, 117.1, 108.8; HRMS (ESI) calcd for $C_{19}H_{11}ONCl^+$ ($M^+$-$BF_4^-$) 304.0524, found 304.0520.

j) 1-(4-(dimethylamino)phenyl)benzo[a]oxazolo[4,3,2-cd]indolizin-10-ium tetrafluoroborate (3n)

Reddish solid, 82% yield; mp=242-244° C.; $R_f$=0.5 (DCM/MeOH=95/10); $^1$H NMR (400 MHz, DMSO-$d_6$) δ=8.78 (d, J=6.8 Hz, 2H), 8.75-8.61 (m, 2H), 8.45 (d, J=8.3 Hz, 1H), 8.21-8.10 (m, J=8.8 Hz, 2H), 8.05 (t, J=7.1 Hz, 1H), 7.97 (d, J=7.3 Hz, 1H), 7.13-6.93 (m, J=8.3 Hz, 2H), 3.18-3.13 (m, 6H); 13C NMR (125 MHz, DMSO-$d_6$) δ=153.1, 152.9, 145.5, 139.8, 134.5, 132.5, 132.1, 129.5, 129.3, 127.2, 125.5, 123.3, 116.7, 116.2, 112.7, 110.0, 106.8, 40.1; HRMS (ESI) calcd for $C_{21}H_{17}ON_2^+$ ($M^+$-$BF_4^-$) 313.1335, found 313.1330.

k) 1-(4-pentanoylphenyl)benzo[a]oxazolo[4,3-cd]indolizin-10-ium tetrafluoroborate (3o)

Off white solid, 53% yield; mp=202-204° C.; R/=0.30 (DCM/MeOH=95/05); $^1$H NMR (500 MHz, DMSO-$d_6$) δ=9.00 (t, J=9.5 Hz, 1H), 8.93 (d, J=7.9 Hz, 1H), 8.81 (dd, J=2.4, 9.2 Hz, 1H), 8.66 (d, J=7.9 Hz, 1H), 8.51 (d, J=8.5 Hz, 2H), 8.41-8.35 (m, 2H), 8.19 (t, J=7.6 Hz, 1H), 8.12 (t, J=7.7 Hz, 1H), 3.17 (t, J=7.3 Hz, 2H), 1.67 (quin, J=7.4 Hz, 2H), 1.43-1.37 (m, 2H), 0.95 (t, J=7.4 Hz, 3H); $^{13}$C NMR (125 MHz, DMSO-$d_6$) δ=199.4, 150.8, 143.9, 139.7, 133.0, 131.9, 131.8, 131.6, 129.7, 128.1, 127.8, 126.4, 126.1, 125.0, 124.1, 123.3, 110.7, 110.7, 38.1, 25.8, 21.8, 13.9; HRMS (ESI) calcd for $C_{24}H_{20}O_2N^+$ ($M^+$-$BF_4^-$) 354.1489, found 354.1485.

l) 1-(2-methoxyphenyl)benzo[a]oxazolo[4,3,2-cd]indolizin-10-ium tetrafluoroborate (3p)

Light yellow solid, 72% yield; mp=228-229° C.; $R_f$=0.50 (DCM/MeOH=95/10); $^1$H NMR (400 MHz, DMSO-$d_6$) δ=8.92-8.81 (m, 2H), 8.78 (d, J=7.3 Hz, 1H), 8.59 (dd, J=3.7, 5.5 Hz, 1H), 8.33 (d, J=7.9 Hz, 1H), 8.13 (d, J=7.9 Hz, 1H), 8.11-8.03 (m, 1H), 8.03-7.94 (m, 1H), 7.84 (t, J=7.9 Hz, 1H), 7.53 (d, J=8.5 Hz, 1H), 7.38 (t, J=7.6 Hz, 1H), 4.14 (s, 3H); $^{13}$C NMR (100 MHz, DMSO-$d_6$) δ=157.5, 147.4, 146.3, 142.2, 135.8, 135.3, 133.9, 132.3, 130.2, 129.9, 128.4, 126.9, 125.8, 121.8, 116.5, 113.6, 112.9, 108.2, 56.5; HRMS (ESI) calcd for $C_{20}H_{14}O_2N^+$ ($M^+$-$BF_4^-$) 300.1019, found 300.1017.

m) 1-(3-methoxyphenyl)benzo[a]oxazolo[4,3,2-cd]indolizin-10-ium tetrafluoroborate (3q)

Light yellow solid, 82% yield; mp=206-208° C.; $R_f$=0.60 (DCM/MeOH=95/10); $^1$H NMR (400 MHz, DMSO-$d_6$) δ=8.99-8.69 (m, 4H), 8.64 (br. s., 1H), 8.23-8.02 (m, 2H), 7.97 (d, J=7.3 Hz, 1H), 7.86-7.65 (m, 2H), 7.52-7.28 (m, 1H), 3.99 (br. s., 3H); $^{13}$C NMR (100 MHz, DMSO-$d_6$) δ=160.3, 150.1, 146.3, 142.7, 135.8, 134.0, 132.8, 132.0, 131.1, 126.9, 126.0, 125.8, 124.5, 120.5, 120.3, 119.9, 119.5, 117.0, 111.8, 108.7, 55.8; HRMS (ESI) calcd for $C_{20}H_{14}O_2N^+$ ($M^+$-$BF_4^-$) 300.1019, found 300.1017.

n) 1-(3-chlorophenyl)benzo[a]oxazolo[4,3,2-cd]indolizin-10-ium tetrafluoroborate (3r)

Off white solid, 58% yield; mp=204-206° C.; $R_f$=0.30 (DCM/MeOH=95/05); $^1$H NMR (400 MHz, DMSO-$d_6$) δ=8.99 (t, J=9.5 Hz, 1H), 8.83 (d, J=7.8 Hz, 1H), 8.77 (d, J=8.8 Hz, 1H), 8.65 (d, J=7.3 Hz, 1H), 8.45-8.27 (m, 2H), 8.18 (t, J=7.6 Hz, 1H), 8.11 (t, J=7.6 Hz, 1H), 7.93 (q, J=7.8 Hz, 2H); $^{13}$C NMR (100 MHz, DMSO-$d_6$) δ=150.7, 150.3, 143.8, 135.1, 133.4, 133.0, 132.6, 131.9, 131.7, 131.5, 126.9, 126.7, 126.4, 126.2, 126.0, 125.0, 122.9, 110.7, 110.6; HRMS (ESI) calcd for $C_{19}H_{11}ONCl^+$ ($M^+$-$BF_4^-$) 304.0524, found 304.0521.

o) 6-methyl-1-phenylbenzo[a]oxazolo[4,3,2-cd]indolizin-10-ium tetrafluoroborate (3s)

Off white solid, 85% yield; mp=220-221° C.; $R_f$=0.30 (DCM/MeOH=95/05); $^1$H NMR (500 MHz, DMSO-$d_6$) δ=8.88 (t, J=8.2 Hz, 1H), 8.78 (d, J=7.6 Hz, 1H), 8.66 (d, J=8.4 Hz, 2H), 8.36 (d, J=7.2 Hz, 2H), 8.01 (t, J=7.8 Hz, 1H), 7.91-7.80 (m, 4H), 2.99 (s, 3H); $^{13}$C NMR (125 MHz, DMSO-$d_6$) δ=150.2, 146.4, 142.5, 137.9, 135.6, 133.3, 132.7, 132.6, 132.4, 130.5, 127.6, 127.0, 124.6, 122.1, 121.3, 118.4, 108.4, 19.4; HRMS (ESI) calcd for $C_{20}H_{14}ON^+$ ($M^+$-$BF_4^-$) 284.1070, found 284.1067.

p) 7-methyl-1-phenylbenzo[a]oxazolo[4,3,2-cd]indolizin-10-ium tetrafluoroborate (3t)

Off white solid, 76% yield; mp=224-226° C.; $R_f$=0.40 (DCM/MeOH=95/05); $^1$H NMR (500 MHz, DMSO-$d_6$) δ=8.89 (t, J=8.2 Hz, 1H), 8.78 (d, J=7.6 Hz, 1H), 8.66 (d, J=8.4 Hz, 2H), 8.36 (d, J=7.2 Hz, 2H), 8.01 (t, J=7.8 Hz, 1H), 7.90-7.82 (m, 4H), 2.99 (s, 3H); 13C NMR (125 MHz, DMSO-$d_6$) δ=149.8, 146.4, 142.6, 141.6, 135.8, 134.2, 133.6, 133.2, 130.5, 127.5, 126.0, 124.7, 124.6, 124.2, 121.1, 116.8, 108.5, 21.5; HRMS (ESI) calcd for $C_{20}H_{14}ON^+$ ($M^+$-$BF_4^-$) 284.1070, found 284.1067.

q) 7-fluoro-1-phenylbenzo[a]oxazolo[4,3,2-cd]indolizin-10-ium tetrafluoroborate (3u)

Off white solid, 65% yield; mp=255-256° C.; $R_f$=0.60 (DCM/MeOH=95/10); $^1$H NMR (400 MHz, DMSO-$d_6$) δ=9.02-8.84 (m, 3H), 8.80 (dd, J=2.1, 8.9 Hz, 1H), 8.70 (d, J=8.5 Hz, 1H), 8.46-8.29 (m, 2H), 7.98 (dt, J=2.4, 8.9 Hz, 1H), 7.92-7.76 (m, 3H); $^{13}$C NMR (100 MHz, DMSO-$d_6$) δ=164.2-161.7 (d, J=250.16 Hz), 150.3, 146.3, 142.6, 135.9, 135.8, 135.1-135.1 (d, J=3.83 Hz), 133.4, 130.5, 127.6, 126.7-126.6 (d, J=9.59 Hz), 124.4, 123.6, 120.5, 120.5-120.2 (d, J=23.96 Hz), 117.7, 113.2-112.9 (d, J=25.88 Hz), 109.3; HRMS (ESI) calcd for $C_{19}H_{11}ONF^+$ ($M^+$-$BF_4^-$) 288.0819, found 288.0815.

r) 7-chloro-1-phenylbenzo[a]oxazolo[4,3,2-cd]indolizin-10-ium tetrafluoroborate (3v)

off white solid, 56% yield; mp=208-210° C.; $R_f$=0.35 (DCM/MeOH=95/05); $^1$H NMR (400 MHz, DMSO-$d_6$) δ=9.09-8.80 (m, 4H), 8.68 (d, J=3.4 Hz, 1H), 8.39 (d, J=6.8 Hz, 2H), 8.16 (d, J=8.3 Hz, 1H), 7.87 (d, J=6.4 Hz, 3H); $^{13}$C NMR (100 MHz, DMSO-$d_6$) δ=150.8, 146.3, 142.8, 140.9, 135.6, 135.3, 134.8, 133.6, 132.4, 130.5, 128.0, 127.8, 125.9, 125.6, 124.4, 120.6, 117.7, 109.4; HRMS (ESI) calcd for $C_{19}H_{11}ONCl^+$ ($M^+$-$BF_4^-$) 304.0524, found 304.0517.

s) 8-chloro-1-phenylbenzo[a]oxazolo[4,3,2-cd]indolizin-10-ium tetrafluoroborate (3w)

Off white solid, 52% yield; mp=206-208° C.; $R_f$=0.30 (DCM/MeOH=95/05); $^1$H NMR (400 MHz, DMSO-$d_6$) δ=8.99-8.78 (m, 4H), 8.68 (d, J=3.4 Hz, 1H), 8.39 (d, J=6.8 Hz, 2H), 8.16 (d, J=8.3 Hz, 1H), 7.87 (d, J=6.4 Hz, 3H); $^{13}$C NMR (100 MHz, DMSO-$d_6$) δ=151.3, 146.3, 142.8, 137.7, 135.0, 133.7, 132.5, 131.2, 130.6, 128.4, 128.1, 127.3, 124.3, 120.4, 117.3, 108.9; HRMS (ESI) calcd for $C_{19}H_{11}ONCl^+$ ($M^+$-$BF_4^-$) 304.0524, found 304.0533.

t) 1-phenyldibenzo[a,f]oxazolo[4,3,2-cd]indolizin-12-ium tetrafluoroborate (3x)

White solid, 72% yield; mp=258-259° C.; $R_f$=0.5 (DCM/MeOH=95/10); $^1$H NMR (500 MHz, DMSO-$d_6$) δ=9.30 (s, 1H), 9.06 (d, J=8.0 Hz, 1H), 8.81-8.77 (m, 1H), 8.77-8.73 (m, 1H), 8.69 (d, J=8.4 Hz, 1H), 8.45-8.42 (m, 2H), 8.35-8.30 (m, 1H), 8.30-8.24 (m, 1H), 8.09-8.01 (m, 2H), 7.90-7.86 (m, 2H), 7.82 (d, J=7.2 Hz, 1H); $^{13}$C NMR (125 MHz, DMSO-$d_6$) δ=148.3, 145.7, 138.1, 134.4, 134.1, 132.6, 132.1, 131.4, 130.6, 130.4, 129.7, 127.1, 127.0, 126.9, 125.3, 124.8, 124.8, 123.6, 122.0, 116.7, 113.9; HRMS (ESI) calcd for $C_{23}H_{14}ON^+$ ($M^+$-$BF_4^-$) 320.1070, found 320.1071.

u) 6-(2-chloro-5-methoxyphenyl)-4H-pyrido[2,1-a]isoquinolin-4-one (3y")

Yellow solid, 62% yield; mp=186-187° C.; $R_f$=0.40 (Pet. Ether/EtOAc=70/30); $^1$H NMR (500 MHz, CDCl$_3$) δ=7.89 (d, J=7.6 Hz, 1H), 7.76 (d, J=7.2 Hz, 1H), 7.56-7.47 (m, 2H), 7.41 (dd, J=6.9, 8.8 Hz, 1H), 7.34-7.28 (m, 2H), 6.83 (dd, J=3.1, 8.8 Hz, 1H), 6.74 (d, J=6.5 Hz, 1H), 6.60 (d, J=2.7 Hz, 1H), 6.49 (d, J=9.2 Hz, 1H), 3.75 (s, 3H); $^{13}$C NMR (125 MHz, CDCl$_3$) δ=159.7, 156.4, 145.0, 137.7, 136.4, 135.6, 134.8, 130.5, 130.0, 129.2, 128.5, 125.5, 120.5, 120.3, 119.7, 116.5, 114.7, 112.2, 99.0, 55.4; HRMS (ESI) calcd for $C_{20}H_{15}O_2NCl$ ($M^+$+H) 336.0784, found 336.0779.

v) (E)-6-(3-chloro-4-methylbenzylidene)pyrido[2,1-a]isoindol-4(6H)-one (3z")

Yellow solid, 23% yield; mp=194-195° C.; $R_f$=0.35 (Pet. Ether/EtOAc=60/20); $^1$H NMR (500 MHz, CDCl$_3$) δ=9.34 (s, 1H), 7.54 (s, 1H), 7.51-7.42 (m, 6H), 7.40 (d, J=7.2 Hz, 1H), 7.14 (d, J=8.4 Hz, 1H), 7.02 (d, J=8.0 Hz, 1H), 6.76 (d, J=6.5 Hz, 1H), 6.64 (d, J=9.2 Hz, 1H), 2.42 (s, 3H); $^{13}$C NMR (125 MHz, CDCl$_3$) δ=163.0, 143.9, 139.5, 137.9, 137.6, 135.9, 131.9, 131.0, 130.0, 129.1, 128.7, 127.9, 123.8, 123.2, 120.5, 120.1, 98.5, 21.6; HRMS (ESI) calcd for $C_{20}H_{14}ONCl$ ($M^+$) 319.0680, found 319.0675.

Example 4: Bioimaging Studies of Pyridinium-Oxazole Dyad Salt 3n in MCF-7 Cells

Materials:
MCF-7 cells are obtained from National Centre for Cell Science, Pune, India. Dulbecco's modified eagle medium (DMEM), Dulbecco's phosphate buffered saline (DPBS), fetal bovine serum (FBS), MTT (3-(4,5-dimethylthiazol-2-yl)-2,5-diphenyl tetrazolium bromide) and DAPI are purchased from Sigma-Aldrich, USA.

Sample Preparation for In Vitro Studies:
The stock solutions (5 mM) of the organic molecules are prepared in DMSO solvent. Each time, the freshly prepared stock solutions are used for all the cell culture experiments.

Cell Culture:
MCF-7 cells were obtained from National Centre for Cell Science, Pune, India. For bio imaging purpose, the cells were seeded in a 6 well plate at a density of $10^5$ cells/mL in Dulbecco's Modified Eagle's Medium+Ham's F12 containing 10% fetal bovine serum and a 0.1% antibiotic solution for 24 h at 370 C and 5% CO2 for adherence Cell Viability Assay:
Cell viability assay was performed in MCF-7 cells using MTT (3-(4,5-dimethylthiazol-2-yl)-2,5-diphenyl tetrazolium bromide) reagent. Compounds at concentration of 1, 5, 10 and 20 µM dissolved in DMSO were added to the cells in media without FBS. DMSO was used as a control. MTT assay was carried out after 24 h incubation. A MTT solution (20 µl, 5 mg/mL) was prepared in PBS pH 7.4 then added to each well and incubated for 3 h. The purple formazan crystals formed were dissolved by addition of 150 µl of DMSO for 5 min absorbance was measured using Biotek SYNERGY HT, microplate reader. $IC_{50}$ was determined by using ED50V10 excel add-on software. Finally, the absorbance of solution was measured using a multimode reader (Biotek Synergy) at 570 nm.

Figure 2:
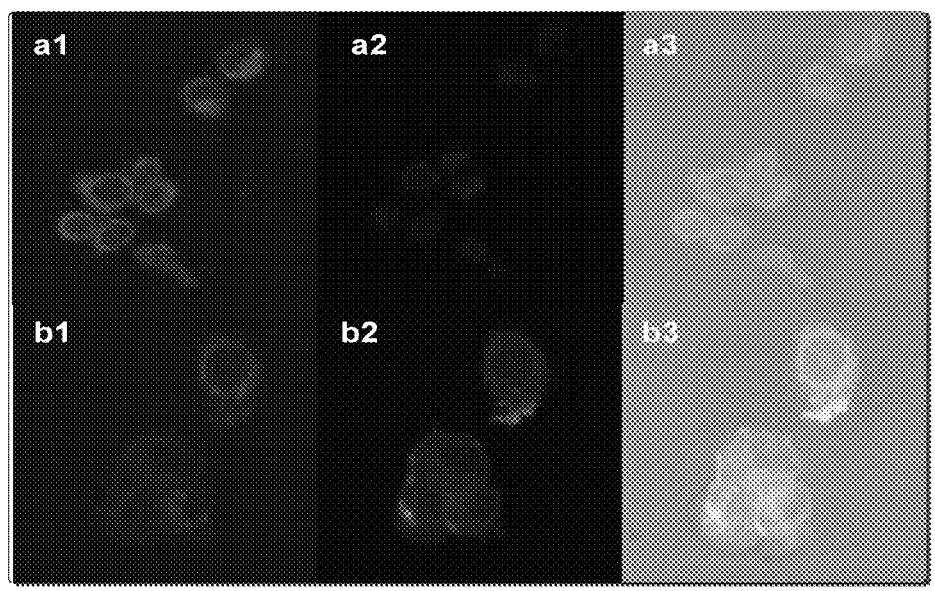
FIG. 2: In vitro imaging in MCF-7 cells. (a1 and b1): MCF-7 cells treated with 1 μM 3h for 6 h; Scale bar=64 and 100 micron. (a2): MCF-7 cells treated with 1 μM DAPI for 6 h; Scale bar=64 micron. (b2): MCF-7 cells treated with 1 μM Mito Tracker Green (MG) for 1 h; Scale bar=100 micron. (a3): merging of red (a1) and blue (a2) fluorescence images of cells. (b3): merging of red (b1), green (b2) fluorescence images of cells and fluorescence images with DAPI

In Vitro Imaging:
MCF-7 cells ($1\times10^4$ cells/mL/well) were seeded in a 6-well tissue culture plate for 48 h. The cells were then treated with 1 µM concentration of different organic molecules for 30 minutes. After thorough washing with 1×PBS ($P^H$ 7.4), the cells are fixed used paraformaldehye (4% in PBS) for 15 minutes. Then cells were washed using 1×PBS twice. Further cells are permeated using 0.4% triton X in PBS for 30 seconds followed by treatment with 1 µg/mL of DAPI solution for 15 minutes. The cells are again ished twice with 1×PBS ($P^H$ 7.4). Finally, a confocal fluorescence microscope (Nikon Eclipse: TE 2000-E, Japan). Bioimaging studies are carried out using red and green filters. (FIG. 2)

Example 5: Co-Staining Experiment with Standard Mitotracker Green (MG)

Cells are cultured and maintained as described above. Cells were treated with 1 µM compound for 30 min followed by washing with PBS. Further cells were treated with 50 nm MG for 10 min and then washed with PBS. Cells were fixed and treated with DAPI as described above.

Example 6: Assessment of 3n for its Ability to Localize and Stain Mitochondria in Living Cells MCF-7 cells were incubated with 1 µM of 3n for 1 h, and excess dyes were washed away by buffer solution. As shown in FIG. 2 (a1 and b1), 3n stains specifically the mitochondrial region in MCF-7 cells. The costaining experiment with MitoTracker green MG (MT), a commercially available mitochondria imaging agent, suggests that the observed fluorescence from 3n is localized in the mitochondria of the living MCF-7 cells (FIG. 2). This study suggests that the 3n can successfully be exploited as an imaging agent for mitochondrial targeting.

ADVANTAGES OF THE INVENTION

1. This is first method for preparation of pyridinium-oxazole dyad salts.
2. These are new class of fluorescent molecules.
3. These class of molecules can be used as mitochondria tracker in live cells.
4. These ionic salts can be used as dopants in organic light emitting diods cells.

We claim:
1. A pyridine compound of formula (II),

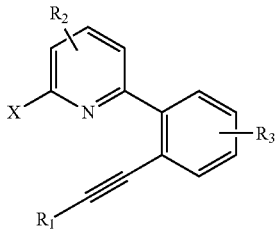

Formula (II)

wherein $R_1$, $R_2$ and $R_3$ are same or different and each is independently selected from the group consisting of H, alkyl groups, alkenyl groups, aryl groups, heteroaryl groups, electron donating as well as electron withdrawing substituents;
X is selected from the group consisting of alkyl, benzyl, aryl, —OR, —SR and —NR, wherein X is not methyl; wherein R is selected from the group consisting of H, alkyl and aryl.

2. A process for the preparation of pyridine compound of formula (II) as claimed in claim 1, wherein the process comprising the steps of:
 a) providing a reaction mixture consisting of a pyridine derivative and a boronic acid in a suitable solvent;
 b) degassing the reaction mixture of step a) with nitrogen;
 c) adding sodium carbonate or potassium carbonate, Palladium catalyst to the reaction mixture of step a) under continuous flow of nitrogen;
 d) heating the reaction mixture of step c) at the temperature ranging from 70 to 80° C. for 4 to 10 hours to obtain the pyridine compound of formula (II).

3. The process as claimed in claim 2, wherein said boronic acid of step (a) is 2 allkynyl phenyl boronic acid and said solvent of step (a) is DMF/$H_2O$ in a ratio of 1:1 and said catalyst of step (b) is $PdCl_2(PPh_3)_2$.

4. The pyridine compound of formula (II) as claimed in claim 1 wherein the compound is selected from the group consisting of:
2-(tert-butoxy)-6-(2-(phenylethynyl)phenyl)pyridine,
2-(tert-butoxy)-6-(2-(naphthalen-1-ylethynyl)phenyl) pyridine,
2-(tert-butoxy)-6-(2-(naphthalen-5 2-ylethynyl)phenyl) pyridine,
2-(tert-butoxy)-6-(2-(phenanthren-9-ylethynyl)phenyl) pyridine,
2-(tert-butoxy)-6-(2-(hept-1-yn-1-yl)phenyl)pyridine,
2-(tert-butoxy)-6-(2-(cyclohex-1-en-1-ylethynyl)phenyl) pyridine,
2-(tert-butoxy)-6-(2-(p-tolylethynyl)phenyl)pyridine,
2-(tert-butoxy)-6-(2-((4-isopropylphenyl)ethynyl)phenyl) pyridine,
2-(tert-butoxy)-6-(2-((4-pentylphenyl)ethynyl)phenyl) pyridine,
2-(tert-butoxy)-6-(2-((4-methoxyphenyl)ethynyl)phenyl) pyridine,
2-(tert-butoxy)-6-(2-((4-butoxyphenyl)ethynyl)phenyl) pyridine,
2-(tert-butoxy)-6-(2-((4-fluorophenyl)ethynyl)phenyl) pyridine,
2-(tert-butoxy)-6-(2-((4-chlorophenyl)ethynyl)phenyl) pyridine,
4-((2-(6-(tert-butoxy)pyridin-2-yl)phenyl)ethynyl)-N,N-dimethylaniline,
1-(4-((2-(6-(tertbutoxy)pyridin-2-yl)phenyl)ethynyl)phenyl)pentan-1-one,
2-(tert-butoxy)-6-(2-((2-methoxyphenyl)ethynyl)phenyl) pyridine,
2-(tert-butoxy)-6-(2-((3-methoxyphenyl)ethynyl)phenyl) pyridine,
2-(tert-butoxy)-6-(2-((3-chlorophenyl)ethynyl)phenyl) pyridine,
2-(tert-butoxy)-6-(2-methyl-6-(phenylethynyl)phenyl) pyridine,
2-(tert-butoxy)-6-(5-methyl-2-(phenylethynyl)phenyl) pyridine,
2-(tert-butoxy)-6-(5-fluoro-2-(phenylethynyl)phenyl) pyridine,
2-(tert-butoxy)-6-(5-chloro-2-(phenylethynyl)phenyl) pyridine,
2-(tert-butoxy)-6-(4-chloro-2-(phenylethynyl)phenyl) pyridine,
1-methoxy-3-(2-(phenylethynyl)phenyl)isoquinoline,
2-(tert-butoxy)-6-(2-((2-chloro-5-methoxyphenyl)ethynyl)phenyl)pyridine,
2-(tert-butoxy)-6-(2-((3-chloro-4-methylphenyl)ethynyl) phenyl)pyridine, and
2-(tert-butoxy)-6-(3,5-dimethoxy-2-(phenylethynyl)phenyl)pyridine.

* * * * *